United States Patent [19]

Walker

[11] Patent Number: 4,545,966

[45] Date of Patent: Oct. 8, 1985

[54] CUPROUS ALUMINUM CYANO TRICHLORIDE: CUAl(CN)Cl$_3$: ITS PREPARATION AND USE FOR THE REVERSIBLE COMPLEXING OF UNSATURATED LIGANDS

[76] Inventor: David G. Walker, 904 Fleetwood Dr., Baytown, Tex. 77520

[21] Appl. No.: 535,165

[22] Filed: Sep. 23, 1983

[51] Int. Cl.$^4$ ............................................. C01B 21/18
[52] U.S. Cl. ................................. 423/245; 260/438.1; 423/246; 423/383; 585/845; 556/27
[58] Field of Search ................... 423/371, 383, 245 R, 423/245 S, 246; 585/845, 849; 260/438.1

[56] References Cited

U.S. PATENT DOCUMENTS

| | | | |
|---|---|---|---|
| 2,338,600 | 1/1944 | Robey et al. | 423/245 |
| 3,026,172 | 3/1962 | Hirschbeck et al. | 585/845 |
| 3,357,789 | 12/1967 | Hunter et al. | 260/438.1 |
| 3,420,862 | 1/1969 | Long | 260/438.1 |
| 3,514,488 | 5/1970 | Uebele et al. | 260/438.1 |
| 3,538,134 | 11/1970 | Tedeschi et al. | 260/438.1 |
| 3,630,676 | 12/1971 | Davis et al. | 423/246 |
| 3,809,726 | 5/1974 | Horowitz et al. | 260/438.1 |
| 3,923,958 | 12/1975 | Turnbo et al. | 423/246 |
| 3,960,910 | 6/1976 | Sudduth et al. | 423/245 |
| 4,279,874 | 7/1981 | Doyle | 423/246 |

OTHER PUBLICATIONS

Kirk–Othmer, *Encyclopedia of Chemical Technology*, 3rd Edition, vol. 4 (1978), pp. 788–793.

*Primary Examiner*—John Doll
*Assistant Examiner*—Wayne A. Langel

[57] ABSTRACT

An aromatic solution of the compound CuAl(CN)Cl$_3$ alone or with additional solid CuAl(CN)Cl$_3$ is used for the separation of some unsaturated compound (olefin, acetylene or carbon monoxide) from a feedstream.

The feedstream is contacted with the solvent to form a complex of the ligand (olefin, acetylene or carbon monoxide). The feedstreem is then separated from the solvent. The solvent is then treated with some combination of heat and lowered pressure to separate the ligand from the solvent. The ligand poor solvent is then recycled to contact fresh feedstream.

5 Claims, No Drawings

CUPROUS ALUMINUM CYANO TRICHLORIDE: CUAL(CN)CL$_3$: ITS PREPARATION AND USE FOR THE REVERSIBLE COMPLEXING OF UNSATURATED LIGANDS

BACKGROUND OF THE INVENTION

This invention relates to the general use of solvents to separate unsaturated compounds (olefins, acetylenes, aromatics and carbon monoxide) from saturated hydrocarbons (paraffins or naphthenes), hydrogen, carbon dioxide, oxygen or nitrogen.

1,3-butadiene was commercially produced by solvent separation as long as forty years ago. (C. E. Morrell et al, Trans. Amer. Institute of Chem. Engs. 1946 pp 473–494). Carbon monoxide is produced commercially in a number of installations using a solvent of CuAlCl$_4$ in toluene. (pages 788-93 of the *Encyclopedia of Chemical Technology* 3rd Edition vol. 4 and the references cited therein).

Many patents have been taken out which claim different solvents for the separation of olefins from various feedstreams. A number of patents claim a solution of CuAlCl$_4$ in aromatics for this use.

A solution of CuAlCl$_4$ in aromatics has many favorable characteristics for a separation solvent. Among these are heat stability, good heat and mass transfer rates along with a high solubility of olefins and acetylenes at relatively low pressure at ambient temperatures. In spite of the many good properties of CuAlCl$_4$, no commercial acceptance has yet occurred for the separation of olefins and acetylenes. Intrinsic catalytic properties of CuAlCl$_4$ (which may be largely prevented by the use of certain additives as reaction inhibitors) have so far prevented the successful commercialization of this technology. (D. G. Walker, *Solid and Liquid Phases Containing CuAlCl$_4$* Div. of Petroleum Chem. ACS 28 no. 3 746-55 Seattle March 1983).

SUMMARY OF THE INVENTION

An addition compound Cuprous Aluminum Cyano trichloride has been discovered to exist. It may be made by the reaction of the two salts cuprous cyanide and aluminum chloride. The compound has a high solubility in aromatics at ambient temperature while the two parent compounds are nearly insoluble. Aromatic solutions of CuAl(CN)Cl$_3$ dissolve large amounts of unsaturated compounds like ethylene, acetylene, propylene and carbon monoxide at atmospheric pressure and ambient temperature. These rich solutions in unsaturated compounds can be heated and/or lowered in pressure to quantitatively volatilize the dissolved unsaturated compound.

COMPARISON OF CuAl(CN)Cl$_3$ WITH CuAlCl$_4$-AROMATIC SOLUTION

Both have high solubilities (3 to 4 Molar at ambient temperature). Both have very fast mass transfer from gas to liquid phase. The ligand pressure solubility curves are both high but CuAlCl$_4$ possesses a considerably higher solubility for CO and some higher solubility for olefins and acetylenics. Both quickly and quantitatively give off CO, ethylene and propylene with vacuum warming. Intrinsic catalytic properties are much less for CuAl(CN)Cl$_3$ than for CuAlCl$_4$. Experimental equilibrium curves for propylene can be measured on uninhibited phases of CuAl(CN)Cl$_3$ while this is impossible with CuAlCl$_4$ due to relatively fast side reactions.

ILLUSTRATIONS

Having now described the invention the following experimental examples will further illustrate the preparation and use of CuAl(CN)Cl$_3$. No limitations are to be implied from these examples since variations and modifications will be obvious to those skilled in the art.

EXPERIMENT 1

0.59 mol of anhydrous Al$_2$Cl$_6$, 0.69 mol of CuCN and 0.94 mol of toluene were combined under nitrogen atmosphere. The sample was stirred and warmed to 50°–60° C. The solids largely disappeared and a dark-colored liquid phase resulted. The sample was left to cool to ambient temperature for three hours. Some new crystalline solid came out. The supernatant liquid was sampled (2.1 ml weighed 2.62 grams) and mixed with an excess of distilled water. A solid precipitate of CuCN resulted and analyzed 6.5 mmol of copper. The aqueous phase analyzed 19.0 mmol of chloride (or 6.3 mmol AlCl$_3$) Neither Cuprous cyanide nor aluminum chloride have any appreciable solubility in toluene at ambient temperature.

A further aliquote of the supernatant liquid was used with a stirred vessel in a chemical vacuum system to measure the equilibrium solubilities of some ligands and the rate of approach to equilibrium. After the measurements on each ligand the sample was vacuum heated to drive off the dissolved gas (caught in a −184° C. trap) and toluene (caught in a −78° C. trap). Some of the solubility measurements are.

TABLE I

| | Temp. 29–31 C. | |
|---|---|---|
| Ligand | Ligand P in mm Hg | Ligand Solubility mmol/ml |
| CO | 325 | 0.9 |
| CO | 570 | 1.55 |
| C$_2$H$_4$ | 130 | 2.1 |
| C$_2$H$_4$ | 320 | 3.2 |
| C$_3$H$_6$ | 90 | 2.0 |
| C$_3$H$_6$ | 310 | 3.5 |

An external water bath was used to help remove heat of complexation. Equilibrium values were reached in about four minutes.

EXPERIMENT 2

4.74 mmol of anhydrous aluminum chloride by weight was mixed with 2.00 ml of toluene in a tube and attached to a chemical vacuum system. The sample was refluxed 10 to 15 minutes under 0.9 atma of nitrogen. A vacuum was pulled to distill HCl and separate it from the toluene. 0.43 mmol of HCl was measured and discarded. The toluene was returned to the vessel. 10.5 mmol of cuprous cyanide was added under nitrogen blanket. The sample was frozen, evacuated and then stirred at ambient temperature seventeen hours. A dark homogeneous liquid resulted with only a small amount of crystalline solid present. Absorption equilibrium measurements were made as in EXPERIMENT 1. At ambient temperature 0.3 mol CO was dissolved per mol of CuAl(CN)Cl$_3$ at a CO pressure of 300 mm Hg. Ethylene and propylene dissolved between 0.8 and 0.9 mol per mol CuAl(CN)Cl$_3$ at the same pressure. Recovery of the complexed ethylene and propylene by vacuum heating of the sample and traping the −184 C. trap gas measurement was nearly quantitative.

INHIBITORS

Small amounts of impurity compounds always exist in $CuAl(CN)Cl_3$ containing phases. These impurities can occur because of the specific synthesis and use history of the phase. Catalytic side reactions due to these impurities with olefins can be effectively suppressed by the use of from one to fifteen mol percent inhibitor compound on the $CuAl(CN)Cl_3$. These inhibitor compounds include ammonia, alkyl amines, pyridine or substituted pyridine, zincdiaryl, boron triaryl, lead tetraaryl and tin tetraaryl. Other effective inhibitor compounds include addition compounds of the formula $R:AlCl_3$ where R is pyridine, ammonia or some amine.

What is claimed is:

1. The compound cuprous aluminum cyano trichloride of the formula: $CuAl(CN)Cl_3$.

2. A process for the separation of a ligand selected from the group consisting of olefins, acetylenes, and carbon monoxide from a feedstream, comprising the steps of:
   (a) contacting the feedstream with a solution of $CuAl(CN)Cl_3$ in aromatics, and optionally containing solid $CuAl(CN)Cl_3$, to form a reaction mixture which contains a complex of the ligand with $CUAl(CN)Cl_3$;
   (b) separating the reaction mixture from the feedstream;
   (c) separating the ligand complex from the reaction mixture; and
   (d) recycling the solution of $CuAl(CN)Cl_3$, optionally containing solid $CuAl(CN)Cl_3$, to step (a).

3. The process of claim 2 wherein the feedstream contains ethylene, acetylene, propylene, methyl acetylene and propadiene in admixture, and the ligands are complexed all together, separated and produced as a mixture.

4. The process of claim 3 where C-4 olfins are also present in the feedstream and all ligands are separated and produced as a mixture.

5. The process of claim 2 wherein from 1 to 20 mol % of an inhibitor is used with the aromatics solvent of claim 1 to suppress ligand side reactions, said inhibitor being a compound of the formula $R:AlCl_3$ where R is ammonia or an amine or an aryl organometallic compound of zinc, tin, lead, aluminum or boron.

* * * * *